(12) United States Patent
Whiteside (10) Patent No.: US 6,569,202 B2
(45) Date of Patent: May 27, 2003

(54) TRAY AND LINER FOR JOINT REPLACEMENT SYSTEM

(75) Inventor: Leo A. Whiteside, St. Louis, MO (US)

(73) Assignee: Whiteside Biomechanics, Inc., St. Louis, MO (US)

( * ) Notice: Subject to any disclaimer, the term of this patent is extended or adjusted under 35 U.S.C. 154(b) by 0 days.

(21) Appl. No.: 10/025,733

(22) Filed: Dec. 19, 2001

(65) Prior Publication Data

US 2003/0014122 A1 Jan. 16, 2003

Related U.S. Application Data

(60) Provisional application No. 60/280,947, filed on Apr. 2, 2001.

(51) Int. Cl.[7] ................................................. A61F 2/38
(52) U.S. Cl. ............................. 623/20.32; 623/20.28; 623/20.33; 623/20.34
(58) Field of Search ........................... 623/20.28, 20.32, 623/20.33, 20.34

(56) References Cited

U.S. PATENT DOCUMENTS 5,766,260 A   6/1998   Whiteside

OTHER PUBLICATIONS

*Effect of Locking Mechanism on Particle and Fluid Migration through Modular Acetabular Components* Cyna Khalily, MD; Michael G. Tanner, MS; Victor G. Williams II, BS; Leo A. Whiteside, MD.

*Modularity—In a Simple and Complex System; P.F.C.® Modular Total Knee System* Johnson & Johnson Orthopaedics.

Primary Examiner—Bruce Snow
Assistant Examiner—Cheryl Miller
(74) Attorney, Agent, or Firm—Polster, Lieder, Woodruff & Lucchesi, L.C.

(57) ABSTRACT

An orthopedic component for total joint replacement that comprises a metal tray (3) and polymer liner (27), the metal tray having screw holes (7a, 7b) for fixation with screws (9) to bone and a circumferential rim or wall (15) with a smooth inner surface (21). The liner (27) is provided with a flexible sealing ridge (39) around its entire periphery, the sealing ridge being positioned so that it sealingly engages the tray rim so as to form a fluid-tight seal between the liner and the tray. The liner is provided with a locking mechanism comprised of tabs at the longitudinal ends of the liner which engage grooves in the front and rear of the tray. In this manner, the surgeon can readily install the liner within the tray after the tray has been surgically affixed to the resected skeletal structure by angling the liner and inserting a first tab into its respective groove and then by pressing the liner downwardly into the tray so that another tab at the opposite end of the liner engages its respective groove thus positively locking the liner with respect to the tray. Simultaneously with snap locking the liner within the tray, the flexible sealing ridge on the tray seals the liner with respect to the tray.

14 Claims, 4 Drawing Sheets

TRAY AND LINER FOR JOINT REPLACEMENT SYSTEM

CROSS REFERENCE TO RELATED APPLICATIONS

This Non-Provisional application claims priority based on U.S. Provisional Patent Application No. 60/280,947, filed Apr. 2, 2001.

STATEMENT REGARDING FEDERALLY SPONSORED RESEARCH OR DEVELOPMENT

Not applicable.

BACKGROUND OF THE INVENTION

Prosthesis components for replacing large anatomical joints are well known in the art, including knee, shoulder, and ankle replacement systems. For example, knee replacement systems typically include femoral components that replace all or part of the joint surfaces of the end of the femur and tibial components that replace all or part of the upper surface of the tibia. The tibial component typically has two parts, a metal tray or shell that is affixed directly to the upper end of the tibia with bone screws, with cement, or with bone ingrowth into a porous undersurface of the tray, and a polymeric (e.g., polyethylene) liner secured within the tray. The lower end of the femoral component typically rounded lower end that simulates the condylar process of the femur. This condylar surface of the femoral component bears on the upper surface of the liner and permits articulation of the knee. The articulation of the femoral component on the polyethylene liner results in microscopic particles of polyethylene being worn from the liner. The metal trays typically have screw holes which receive bone screws that are anchored into the tibia to enhance immediate fixation. However, these screw holes can cause problems by allowing joint fluid along with the polyethylene debris to be forced into the screw holes under pressure and thus dissolve and destroy the bone structure supporting the tray. Even when occupied by a screw, the screw holes allow joint fluid and debris to migrate around the screw and to come into contact with the underlying bone structure, gradually loosening it and destroying bone.

Some efforts have been made to address these problems in the prior art. The polyethylene liner or component has been locked securely to the metal tray with a peripheral locking flange to prevent up and down motion of the polyethylene component and resultant high pressure pumping of joint fluid into the screw holes. These tight capture mechanisms do not, however, prevent joint fluid from bathing the screws, and in situations in which joint fluid pressure is elevated, such higher levels of joint fluid pressure can be transmitted to the screw holes, thus forcing joint fluid through the screw holes and into the bone proximate the screw holes and resulting in bone loss around screws and under empty screw holes. Over time, this loss of bone supporting the tray jeopardizes the structural integrity of the knee replacement system.

Another approach to minimizing the danger of bone loss is to minimize the wear on the under surface of the polyethylene component by polishing the metal tray. However, it has been found that most of the wear debris is generated at the actual bearing surface between the femoral and tibial joint surfaces, and is not affected by polishing the under surface of the polyethylene component.

Still another approach is to develop tibial trays with no screw holes. While this would eliminate the route of access of joint fluid and debris into the underlying bone, it eliminates the use of screws, which are a desirable or even necessary feature for fixation of the metal tibial tray onto the bone surface, particularly in patients with soft bone.

Reference may be made to my prior U.S. Pat. No. 5,766,260 entitled "Acetabular Component With Improved Liner Seal and Lock", issued Jun. 16, 1998, which disclosed modular acetabular components in a total hip replacement system. In particular, my prior '260 patent disclosed a continuous flexible seal on a part spherical plastic liner which sealingly engaged its part spherical metal shell for continuous 360° sealing around the liner. More specifically, as the liner was installed in its acetabular shell, the liner would flex and would thus make a continuous seal with respect to the shell and a snap-lock securement was provided to secure the part-spherical liner within the part-spherical shell. This acetabular liner was fixedly secured to its shell by means of peripheral tabs on the liner which were received in corresponding notches in the shell, and by means of interlocking ridges extending around the part spherical shell which were received in a continuous interlocking groove on the inner face of the shell.

As reported in a paper entitled "Effect of Locking Mechanism On Particle and Fluid Migration Through Modular Acetabular Components", by Cyna Kalily et al., presented at the 64$^{th}$ Annual Meeting of the American Academy of Orthopaedic Surgeons, Feb. 13–17, 1997, a seal, such as described in the above-noted '260 patent, which was incorporated in the MicroSeal® hip system (similar to that described in my '260 patent) commercially available from Whiteside Biomechanics, Inc., of St. Louis, Mo., was effective in preventing the migration of joint fluid and debris between the liner and the metal shell. Because the continuous seal of the MicroSeal® hip system prevented joint fluid from passing coming into contact with the bone structure under the tray, degeneration of bone structure proximate the bone screws anchoring the shell would be considerably lessened.

As noted above, it has been known that the migration of joint fluid and debris through the screw holes in a tibial tray in a total knee replacement system caused degeneration of the tibia supporting the tibial tray. However, in attempting to incorporate a continuous seal, such as disclosed in the '260 patent, which was only used with a part spherical shell in a tibial tray in a knee replacement system, it was found that continuous peripheral tabs and corresponding continuous notches and the locking ridge/locking groove arrangement disclosed in the '260 patent would not permit a surgeon to snap lock the liner into the tibial tray. This is due to the fact that in knee, ankle, shoulder and other large joint replacement systems, the liner component cannot be laid directly symmetrically on the metal shell (e.g., on the tray) component and pressed into place, as it can be in inserting a liner in an acetabular shell of a hip replacement system. Typically, the liners for such other joint replacement systems must be inserted from the front, side or back because of the presence of tissue, ligaments or the like. Because of the necessity of the front, side or back insertion of the liner into its tray, the surgeon oftentimes cannot apply a load directly to the center of the polymeric liner of sufficient magnitude to drive the liner into place within its tray or shell component. It has also been found that due to the difficultly of inserting such liners into their respective tray or shell components, the close tolerances required to prevent movement of the liner with respect to the tray during usage of the appliance by the patient could not be maintained.

In summary, there has been a long-standing need for a joint replacement component (e.g., a tibial tray) and liner which are of non-spherical or non-circular shape that effectively prevents the migration of joint fluid and debris from the tray to the bone structure receiving the bone screws which secure the tray to the tibia, which maintains the close tolerances needed to rigidly secure the liner within the tray to prevent relative movement, and yet which liner can be readily installed by the surgeon once the component (tray) has been affixed to the tibia.

SUMMARY OF THE INVENTION

Among the several objects and features of the present invention may be noted the provision of a joint replacement component, such as a non-part spherical tibial tray for a knee replacement system, and a non-part-spherical polymeric (polyethylene) liner having a continuous seal integrally formed on the liner and extending completely around the liner for continuously sealing the liner with respect to the tray thereby to prevent the migration of joint fluid and other debris (or contaminants) from the tray to the bone structure supporting the tray via bone screw holes in the tray which is easy for the surgeon to install and which is securely held in place where the liner may be readily snap-locked into place by the surgeon during the surgery;

The provision of such a joint replacement component, such as a tray, in which the liner is positively maintained within the tray such that the seating surfaces of the tray and the liner remain in their desired positions relative to one another even under alternating biomechanical loading during long term use;

The provision of a tibial tray for a knee replacement system which, during installation, allows the liner to be inserted from one side leaving ligaments and capsule in tact on the surfaces that have not been surgically transected;

The provision of such a joint replacement component which provides positive, tactile securement of the liner with the component during installation of the liner so as indicate to the surgeon of complete and proper seating of the liner;

The provision of such a joint replacement system in which the liner component is positively seated with respect to its tray or shell component so as to effectively prevent toggling, rocking, or slipping of the liner with respect to the tray component throughout a range of biomechanical loads and throughout a range of biomechanical movement of the components of the total knee (or other joint) replacement system over the service life of the total joint replacement system;

The provision of such a joint replacement system which minimizes the loss or destruction of the soft bone supporting the tray component due to exposure of the joint to joint fluid seeping or forced into contact with the bone structure via screw holes in the tray or shell component; and The provision of such a joint replacement component which made of materials suitable for implantation, which is of simple and rugged construction, which requires minimal space when installed, which is easy and fast to install, and which has a long service life once installed.

A joint replacement component for a total joint replacement system of the present invention comprises a tray made of a suitable implantable metal. The tray has a base and a wall (or rim) extending upwardly from the base for defining a recess, the recess having a non-circular shape corresponding generally to the non-circular shape of the tray. The base has one or more holes therein for receiving bone fixation fasteners for fixation of the tray with respect to a suitable skeletal structure. A liner of suitable synthetic resin material is provided for securement within the recess after the tray has been surgically affixed to the tibia. The liner has a non-circular shape corresponding generally to the non-circular shape of the recess. The tray wall has an inner wall surface which substantially defines the outer periphery of the recess with the inner wall surface tapering inwardly and downwardly toward the base tray. The inner wall surface has an undercut groove on the opposite end or side of the recess. The liner has a side wall generally of the same non-circular shape as the tray wall and is sized with respect to the tray wall as to fit closely within the inner wall surface such that with the liner installed in the recess of the tray, the liner and the inner wall surface are dimensioned with respect to one another so that with the tray and the liner at body temperature, the liner is securely held within the recess by the tray wall thereby to substantially eliminate movement of the liner with respect to the tray upon subjecting the tibial component to biomechanical loads during normal use of the knee replacement system. The liner side wall has a continuous seal formed integrally with the liner with the seal sealingly engaging the inner wall surface when the liner is installed within the recess thereby to prevent the migration of joint fluid and/or debris past the seal into communication with the holes in the base of the tray. The liner further has at least one locking tab or flange on opposite ends or sides thereof. The locking tabs are preferably integral with the liner and are engageable with the undercut groove in the inner wall surface thereby to snap-lock the liner within the tray as the liner is inserted into the tray by a surgeon after the tray has been surgically affixed to the tibia.

Other objects and features of this invention will be in part apparent and in part pointed out hereinafter.

BRIEF DESCRIPTION OF THE DRAWINGS

FIG. 4 is a top perspective view of the liner component which is adapted to be installed within the recess of the tray shown in FIG. 1 where the upper surface of the liner is somewhat concave so as to permit articulation with femoral component (not shown) of the knee replacement system, where the lower peripheral margin of the liner has a flexible sealing flange extending continuously around the liner for continuously sealingly engaging the inner surface of the rim wall so as to positively seal the liner to the tray and to prevent the migration of joint fluid (or debris) past the seal toward the screw holes in the tray, and where the lower margin of the liner only at the ends of the liner has a locking flange adapted to snap lock with the corresponding locking groove at opposite ends (e.g., the anterior and posterior ends) of the tray walls forming the recess therein;

FIGS. 9A and 9B are enlarged views of a portion of the liner and of the tray as the liner is being snap-locked installed within the tray illustrating how the liner is inserted in the tray at an angle such that one end of the liner is inserted within the tray first with a flange partially installed in its respective groove (see FIG. 9A) and with the other end of the liner bearing against a tapered wall of the tray (see FIG. 9B) such that as the surgeon forcefully pushes the liner down into the tray the liner flange bearing on its respective tapered tray wall slides down the tapered tray wall such that as the liner becomes substantially installed within the tray, the flange on the end of the liner shown in FIG. 9A snaps in place within its respective groove so as to securely hold or lock the liner within the tray;

Corresponding reference characters indicated corresponding parts throughout the several views of the drawings.

DESCRIPTION OF PREFERED EMBODIMENTS

Figure 7:
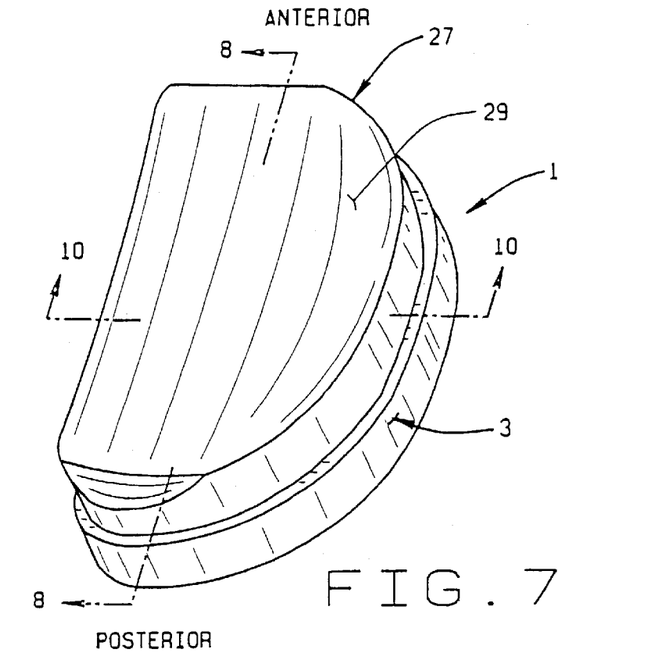
FIG. 7 is a top perspective view of the liner installed in the tibial tray of this invention.

Referring now to the drawings, and particularly to FIG. 7, a prosthesis component for a total joint replacement system of the present invention, namely a tibial component for a knee arthroplasty system, is illustrated in its entirety at 1. Within the broader aspects of this invention, those skilled in the art will recognize that the present invention may be used with a wide variety of orthopedic implant appliances other than tibial components for knee replacement systems and that the components herein described may be affixed to skeletal structures other than the tibia. For example, the features of this invention may be used with an acetabular cup or shell which is surgically affixed to the pelvis in hip replacement surgery. The features of this invention may be also used in total joint replacement systems for the shoulder and the ankle. For the purpose of brevity, the present invention is described in the environment of a total knee replacement system. However, the application of the principles of this invention to other total joint replacement systems (e.g., to total hip, shoulder and ankle joint replacement systems) will be readily apparent to those skilled in the art.

Figures 1, 2:
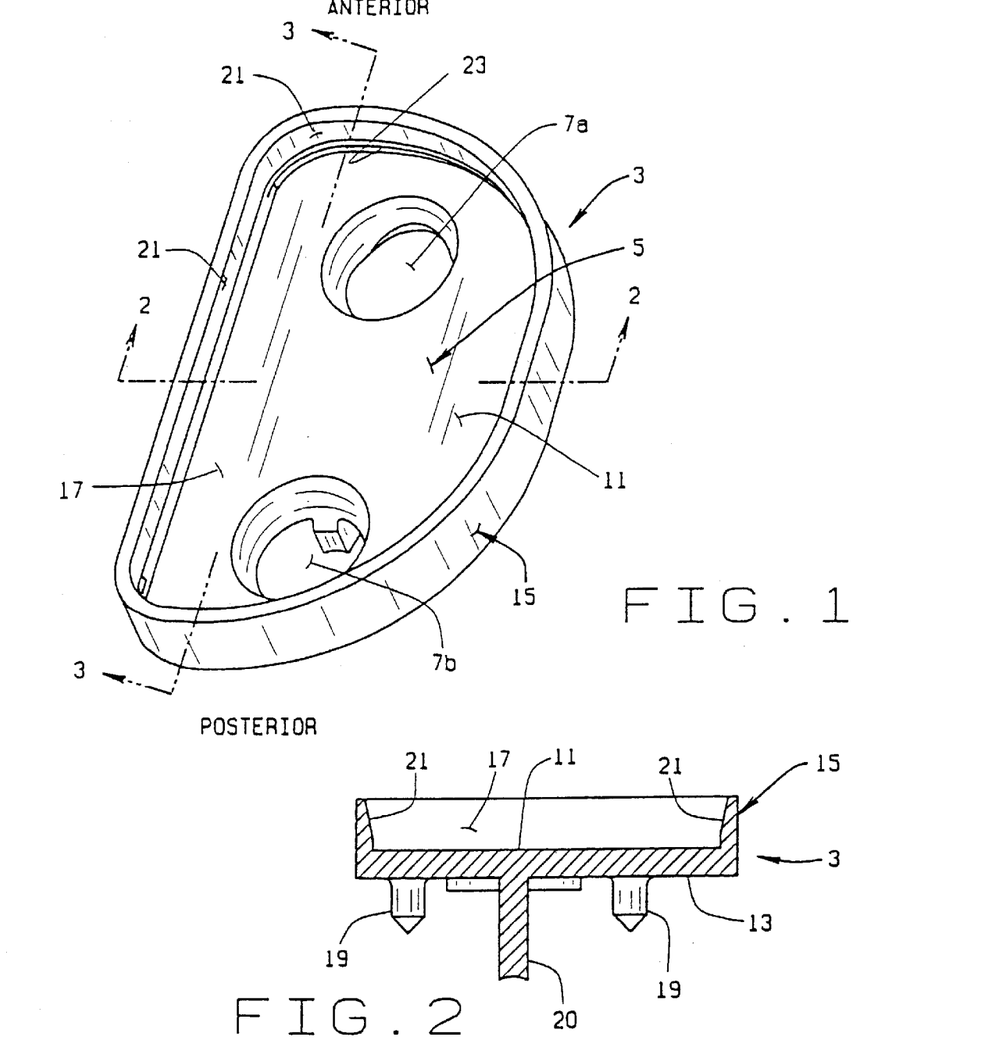
FIG. 1 is a top perspective view of a metal component (e.g., a unicompartmental knee replacement system tibial tray or shell) for a joint replacement system of the present invention having base with a plurality of screw holes therein for the reception of bone screws (not shown) and a rim or wall extending around the base defining a recess therein.
FIG. 2 is a lateral cross sectional view taken along line 2—2 of FIG. 1 illustrating a pair of pointed protrusions and a keel on the bottom face of the tray for reception in corresponding bores or grooves in the upper end of the tibia so as to aid in fixation of the tray with respect to the tibia.
Figure 3:
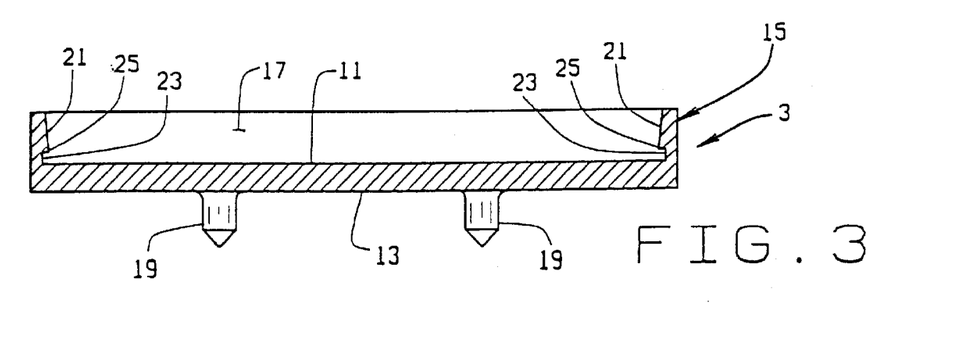
FIG. 3 is a longitudinal cross sectional view taken along line 3—3 of FIG. 1 illustrating that the inner surface of the rim wall tapers inwardly and downwardly toward the base and further illustrating the provision of undercut grooves only in opposite sides or ends of the rim walls (e.g., in the front and rear rim walls, also referred to as the anterior and posterior of the recess) for the snap-lock reception of corresponding securement lugs (as shown in FIGS. 8 and 9) of a liner component installed within the recess of the tray.

Referring now particularly to FIGS. 1–3, the tibial component for a total knee replacement system includes a tibial tray or shell 3 of a suitable metal, such as an annealed titanium (preferably an alloy similar to ASTM F1472, or the like), for being implanted in the human body. As best shown in FIG. 1, tray 3 has a generally flat base 5 and screw holes 7a, 7b for reception of suitable bone screws 9 (as shown in phantom in FIG. 8) for permanent attachment of the tray to the end of the tibia which has been surgically prepared for the tray during the surgery. As best shown in FIG. 2, tray base 5 has an upper surface 11, a lower surface 13, and a peripheral rim or wall 15. The lower surface 13 of the tray is generally flat and is configured to fit the flat upper surface of the tibia after it has been resected to accommodate the tibial component. The peripheral rim 15 extends continuously around the entire periphery of the tray and form a recess 17 within the tray.

Figure 4:
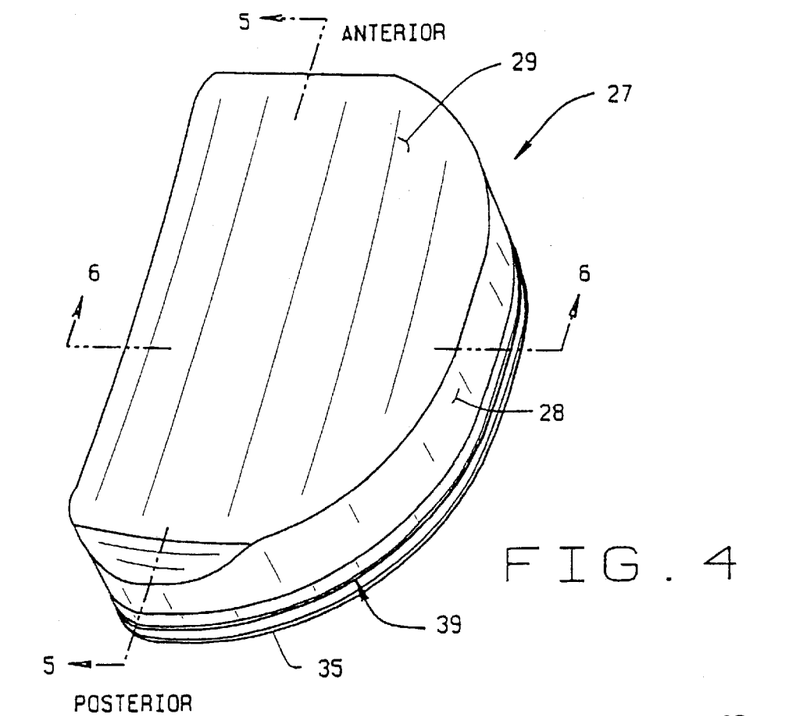

It will be understood that the tibial component 1 of the present invention is reversible so that it may be used on either the left or right leg of a patient. Further, tray 3 has a front or anterior side (as indicated in FIGS. 1, 4, and 7), a back or posterior side (as also indicated in FIGS. 1, 4, and 7), and medial and lateral sides. These references will aid in describing the construction and operation of the tibial component of this invention, but it will be understood that tibial components of this invention may be used in reconstructing either a patient's right or left knee and the used of the above reference terms shall not be in a limiting sense.

As shown in FIGS. 1–3, the lower face of tray 3 has one or more pointed protrusions or pegs 19 for insertion into corresponding bores (not shown) formed in the upper surface of the tibia after resection to resist movement of the tray with respect to the tibia. Likewise, the tray has a downwardly projecting keel 20 which is received in a corresponding groove (also not shown) formed in the flat upper surface of the tibia so as to further aid in fixing the tray with respect to the tibia.

Figures 8, 10:
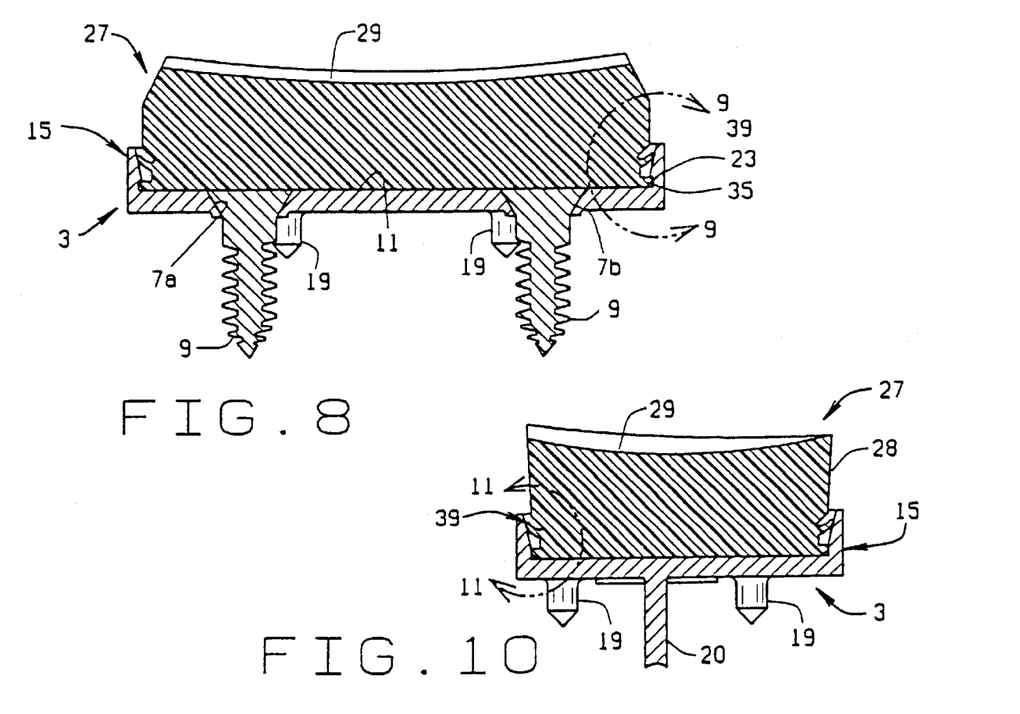
FIG. 8 is a cross sectional view of the liner, as it is installed in the tray, taken along line 8—8 of FIG. 7.
FIG. 10 is a cross sectional view of the liner as it is installed in the tray taken along line 10—10 of FIG. 7.

As indicated generally at 21, the inner wall surface of the peripheral rim 15 is beveled or tapered such that the inner surface of the wall slopes inwardly and downwardly toward the upper face 11 of base 5. At each longitudinal end of the tray, an undercut groove 23 (as best seen in FIG. 10) is cut into the wall 21 proximate upper surface 11 of base 5 for defining a corresponding ledge or shoulder 25. Preferably, taper or bevel extends downwardly along the inner face of the rim to a level just above groove 23 for purposes as will appear. As noted, a groove 23 is provided only at opposite ends (sides of recess 17. As perhaps best shown in FIG. 1, tray 3 is of a noncircular (i.e., it has one dimension longer than the other) curvilinear shape which, when viewed in plan, has a major dimension (as shown by line 3—3) and a minor dimension (as shown by line 2—2). Likewise, rim wall 15 is of a corresponding, non-circular, curvilinear shape extending around the periphery of the tray. The recess 17 formed within tray 3 by rim 15 has a corresponding non-circular shape. As shown in FIG. 1, grooves 23 are only provided only in the ends of the recess corresponding generally to the major dimensions of the tray and grooves are not present at the sides of the recess 17 for purposes as will appear. It will be understood that the tray 3 herein shown is a unicompartmental component and as such the major dimensions extend front-to-back and the minor dimensions extend side-to-side.

While the liner and tray components as herein described are so-called "non-circular" components, it will be understood that within the broader aspects of this invention, the provision of the above described lugs on the liner component and corresponding undercut grooves in the inner surfaces of the tray component rim walls which are provided on opposite sides or ends thereof will aid in the insertion of any liner-like component within its tray or shell component, particularly where a surgeon does not have direct access to drive the liner into its tray and where the liner must be inserted from the front, side, or back.

The tibial tray 3 shown in the drawings is a unicompartmental tibial replacement component and it will be understood that the major dimension extends from front to back relative to the patient and the minor dimension extend from side to side. The tibial component of this invention may also be used with compartmental tibial trays (not shown) in which case the major dimension is from side to side. As previously noted, those skilled in the art will also understand that the present invention may be used with orthopedic appliances other than tibial trays in knee replacement systems and it may be used with such components other than those having a flat base with an upstanding rim. For example, the present invention may be used with an acetabular shell or cup of generally part-spherical shape where the base in the bottom of the spherical recess and the rim is a part of the part-spherical wall of the cup.

Figure 5:
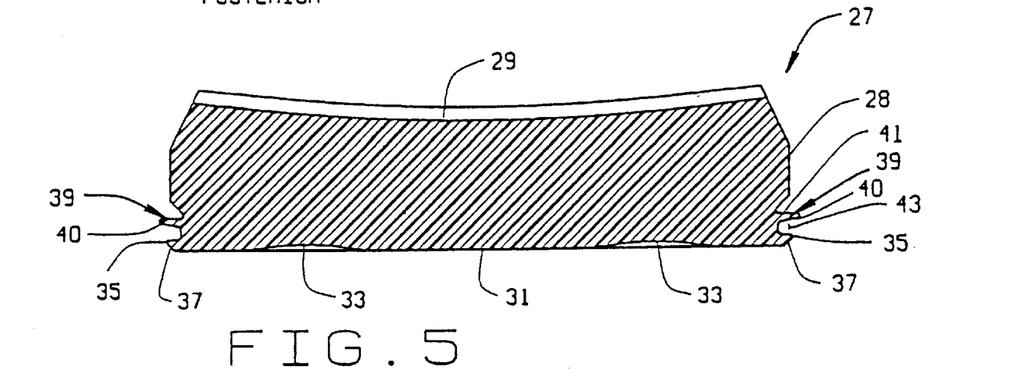
FIG. 5 is a longitudinal cross sectional view of the liner taken along line 5—5 of FIG. 4.
Figure 6:
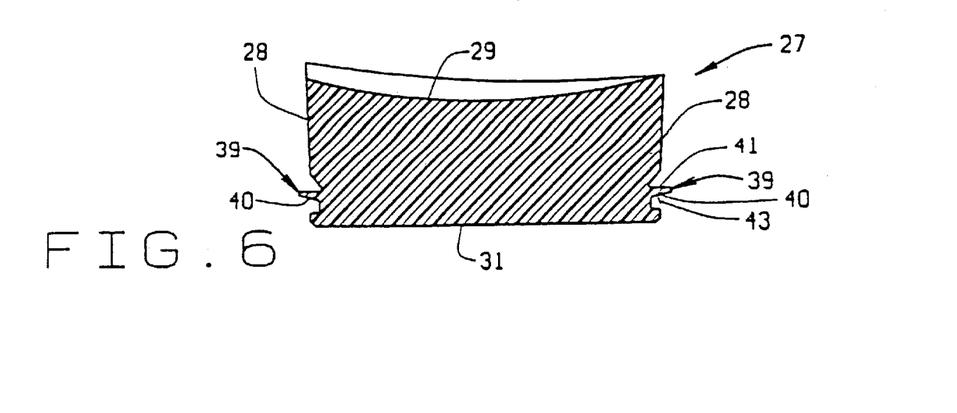
FIG. 6 is a lateral cross sectional view of the liner taken along line 6—6 of FIG. 4.

A liner, as generally indicated at 27 and as best shown in FIGS. 4–6, has a similar non-circular shape and is designed to be inserted (snap-locked) into recess 17 and to have a tight fit with the inner surface of rim 15 when the tray and liner are at body temperature. Liner 27 is machined from a suitable synthetic resin, preferably a premium grade UHMW-PE (Ultra High Molecular Weight Polyethylene) commercially available from Hoescht Cleanse Company and identified as Resin 1050, where the resin conforms to ASTM Specification F648-96.

Liner 27 has a generally vertical side wall 28 that extends around the periphery of the liner. As shown in FIG. 5, liner 27 has a somewhat concave upper surface 29 which simulates the condyle of the tibia and which cooperates with the condylar of the femoral component (not shown) so that the articulation of the knee replacement system simulates the articulation of the human knee. As best shown in FIG. 5, liner 27 further has a lower surface 31 which bears against the upper surface 11 of base 5. The lower surface of the liner is preferably provided with upwardly extending recesses 33 so as to provide clearance for the heads of bone screws 9. As noted, the upper surface 29 of the liner articulates with the smooth metal femoral component to form an artificial knee joint. This upper surface is concave, and is shaped to conform generally to the shape condylar of the femoral component. The liner, which as noted is preferably formed of polyethylene, is slightly deformable (compressible) as it accommodates the curvature of the femoral component upon being subjected to body weight. The liner maximizes the weight-bearing area of the interface between the liner and tibial tray, and resists shear stresses that would cause the two parts to slide on each other and to generate wear debris.

Tray 3 and liner 27 are designed such that with the tray and liner at body temperature, as installed in a patient, the liner will have a snug fit within the tray recess so as to prevent movement of the liner with respect to the tray and so as to prevent wear and deformation of the liner. It will be appreciated that such movement of the liner with respect to the tray may generate particles of debris from wear of the liner that are to be avoided in the knee or joint area. The desired snug fit of liner 27 in recess 17 also aids in preventing rocking or relative movement between the liner and the tray. However, this snug fit, by itself, is insufficient to seal the interface between the liner and tray, and therefore cannot prevent this interface from conducting joint fluid and debris to the screw holes. As noted, the introduction of joint fluid to the bony structure proximate bone screws 9 causes deterioration of the bony structure and can require surgical repair of the tibial prosthesis.

Because of the desired snug fit of liner 27 in recess 17, it is noted that the liner must be dimensioned with respect to tray recess 17 such that only minimum clearance between liner sidewall 28 and the inner wall surface of rim 15. The fact that inner surface 21 of the rim is tapered (as described above) aids in installing the liner within the recess. However, because the liner is formed of solid resin and because it is relatively thick, even though the resin is somewhat resilient, it is not possible for it to be readily deformed sufficiently during manual installation by a surgeon. In accordance with this invention, the liner, formed of the above-noted polyethylene resin, and the tray, formed of titanium, are dimensioned with respect to one another such there is adequate clearance between the liner and the tray rim for ready manual installation of the liner by the surgeon during surgery after the tray has been affixed to the tibia. As the tray and the liner come up to body temperature (98.6° F.), the tray and the liner will expand at different rates because their coefficients of thermal expansion are different. These parts are dimensioned relative to one another such that there is adequate clearance for installation of the liner when the liner is at room temperature (65–72° F.) and when the tray (which has already been surgically affixed to the tibia) is nearly at body temperature. After the liner 27 has been snap-lock inserted into tray recess 17 (in the manner as will hereinafter be described), the liner will come up to body temperature and will thus expand so has to have a tight fit with the inner surface of rim wall 21.

In order to further facilitate the installation of liner 27 in tray recess 17, and in order to fixedly secure the liner to the tray, a snap-lock securement arrangement (sometimes also referred to as an interlock arrangement) between the liner and the tray is, in accordance with this invention, provided preferably only at opposite ends or sides of the tray and the liner.

More particularly, at each longitudinal end (or at each lateral side) of liner 27, a tab or flange 35 extends out beyond the side wall 28 of the liner. Flange 35 has a chamfer 37 (see FIG. 9C) on its lower face and is of a height less than the height of undercut recess or slot 23 in the lower reaches of the rim 15 at the anterior and posterior ends of the tray recess. Thus, the flanges 35 extend out beyond or past the peripheral edge of the liner approximately one millimeter so that they will engage (snap lock into) their respective undercut grooves 23 to prevent the liner from lifting off the inner surface of the tray. Further, the lower, outer edge of the flanges 35 is chamfered, as indicated at 37, to aid in installation of the liner within the tray, as will be hereinafter described. It will be further noted that such flanges are not provided along the other opposed sides of the liner.

Figure 9A:
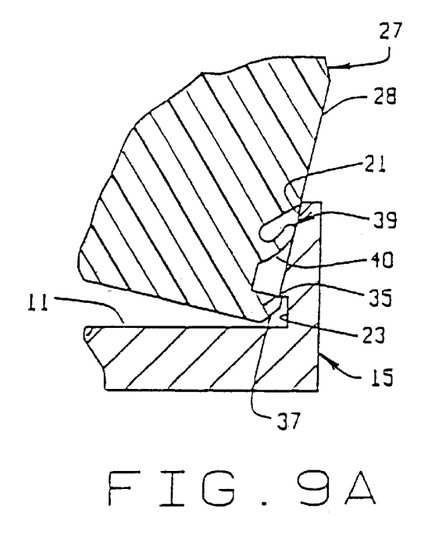
FIG. 9C is a view similar to FIGS. 9A and 9B illustrating the relationship of the liner and the tray at one of the major dimension ends of the tray after the liner has been properly installed within the tray.
Figure 9B:
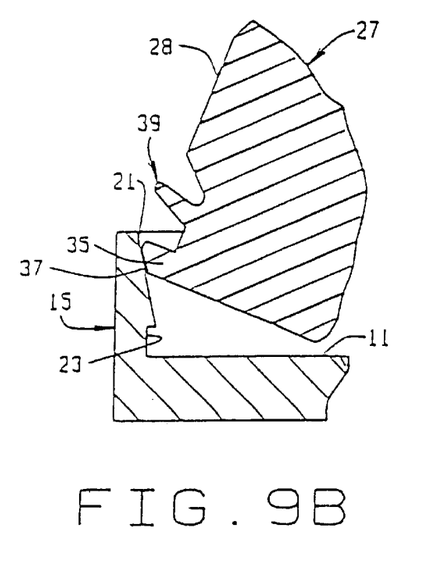
Figure 9C:
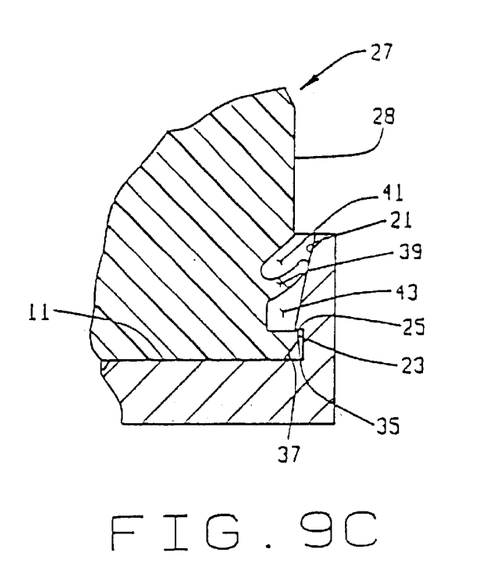
Figure 11:
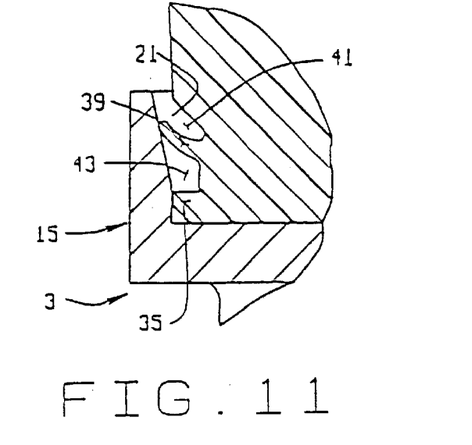
FIG. 11 is a cross sectional view of the liner as it is installed in the tray taken along line 11—11 of FIG. 7 illustrating how the flexible sealing flange of the liner sealingly engages the inner surface of the rim (or wall) and further illustrating that there is no snap-lock securement of the liner to the tray along the longitudinal sides of the recess thereby to more readily permit the surgeon to install the liner within the tray after the tray has been surgically affixed to the tibia.

If the collateral ligament is kept intact during the knee replacement surgery (which is highly desirable), the knee can only be entered surgically from the front. Thus, the liner must be inserted in the tray from front to back, and not inserted from side to side or back to front. However, as pointed out above, with liner 27 made of a solid polyethylene, it is not possible for the surgeon to apply sufficient force so as to deform the liner upon installation because the liner is too stiff. However, with flanges 35 provided on the liner only along two ends of the liner (e.g., along the longitudinal ends of the liner) or along two sides of the liner, the surgeon can angle the liner slightly with respect to the plane of the tray (as shown in FIGS. 9A and 9B) such that the surgeon inserts one flange 35 on the liner into its corresponding recess 23 (as shown in FIG. 9A). With the liner 27 at an angle (as shown in FIG. 9B), the flange 35 at the opposite end of the liner is above its groove 23 and (as shown in FIG. 9B) the chamfer 37 on the opposite flange 35 bears against the inclined portion 21 of the rim 15. As the surgeon may manually push the liner down into the recess in the tray, the flange 35 at the opposite end of the liner (as shown in FIG. 9B) slides down tapered wall 21 of the tray above its groove 23 at that end of the tray. As the surgeon pushes down on the liner, flange 35 will flex a small amount. Further, the bevel 37 on the bottom edge of the liner somewhat shortens the effective length of the liner while it is being installed so as to reduce the force required to push it into the liner. Still further, it will be appreciated that with the tray made of metal (e.g. titanium) and with the liner made of a suitable plastic, such as polyethylene, the coefficient of friction of the liner against the tapered wall 21 of the titanium tray is low and this low coefficient of friction also aids in reducing the force required of the surgeon to install the liner into the tray and facilitates installation of the liner in the tray. As this second flange 35 moves downwardly along tapered wall 21 and as the flange moves into register with its groove 23, the flanges 35 will snap lock into their respective grooves 23 thereby positively retaining the liner within the tray (as shown in FIG. 9C). While flanges 35 and grooves 23 have been described as being along opposite major dimensions of the liner and tray, it will be understood that within the broader aspects of this invention, the flanges and grooves may be disposed along any opposite sides of the tray. By not having such flanges on all sides of the tray, the force required to install the liner into the tray and to snap-lock the liner is place is markedly lessened, and yet, the liner is firmly secured with the tray by providing such flanges and grooves only along two opposite sides thereof.

It should be particularly noted that with the tabs 35 being located only on opposite ends or sides of the liner, this allows the plastic (e.g., polyethylene) component (i.e., the liner) to be inserted into the tray from one side or end and locked in place without placing a driving instrument directly on the center of the plastic component, which, of course, would require excessive exposure. It will be appreciated that in joint replacement or repair surgery, an important is surgical exposure. In knee, ankle, shoulder and other large joint surgery, the plastic component cannot be laid directly symmetrically on the metal shell or tray and then pressed into place. Instead, it must be placed from the front, back or side. Then the surgeon cannot apply a load directly to the center of the plastic (polyethylene) component to drive it into place. This is an important reason that the tabs or flanges 35, as shown above, are placed on opposite side (or at opposite ends) so as to allow the locking tabs on one side to be first located within their respective groove (i.e., to be locked down), and then the load is applied by the load is applied by the surgeon to the side nearest the surgeon, directly in the operating field, to finish driving the locking tabs into their respective grooves and to thus snap lock the liner to the tray. It will be further understood that the above arrangement of the locking tabs being located on opposite sides or ends of the liner and with corresponding grooves in the tray or shell receiving the liner, that this system will work with all shapes of trays and liners (i.e., with part spherical, rectangular, or curvilinear shapes).

After a tibial component of this invention has been surgically installed and as the patient walks, weight-bearing stresses tend to shift during walking. These shifting stresses can loosen the liner 27 within the tray 3 and the shifting stresses can act as a piston trapping joint fluid as it rises and compressing it as it descends with the recess 17 of tray 3. This piston motion can subject the space between the lower face of the liner and the upper surface 11 of the tray base to relatively high pressure joint fluid which, in turn, can force joint fluid and debris carried by the joint fluid past the screws inserted in screw holes 7a, 7b and into the bone surrounding the screws causing loss of bone stock and loosening of the implant. The flange 35 and groove 23 arrangement heretofore described lessens this piston-like movement of the liner relative to the tray, but flange 35 and grooves 23 are insufficient to seal the interface between the tray and liner and to prevent joint fluid and debris from finding their way to the screw holes and to the bone below the tray. Further, in accordance with this invention, flanges 35 are provided only at opposite ends of the liner. Moreover, for the best locking function of the liner within the tray, flanges 35 must be relatively stiff. However, this desired stiffness characteristic of the flanges effectively prevents the flanges from also acting effectively as a seal.

Thus, in accordance with this invention, the liner is provided with a flexible peripheral seal 39 for sealing the liner with respect to the tray and to thus positively prevent the migration of joint fluid and/or debris past the interface between the inner surface of the tray rim wall and the peripheral wall of the liner and into contact with the bone underlying the bottom face of the tray. The seal is carried by the liner and extends completely around the peripheral wall of the liner to provide ease of insertion and to give a continuous seal between the interface of the tray and liner.

As seen in the drawings, flexible seal 39 extends continuously around liner 27 above flange 35 with the seal adapted to sealingly engage in inner surface 21 of rim wall 15 somewhat above the level of undercut grooves 23 provided at the opposite ends of the tray. Seal 39 is shown to have generally a triangular cross section. The seal 39 is defined by an upper groove 41 and a lower groove 43 in liner 27 such that seal 39 is cantilevered from and integral with the main body of liner 27. Preferably, seal 39 angles upwardly a slight amount so as to facilitate installation of the liner within the recess of the tray and to facilitate sealing with respect to the rim. Because liner 27 and seal 39 (which is preferably integrally machined from the main body of the liner) is flexible as the liner is forcefully, manually inserted into recess 17 by a surgeon during surgery, the outer end of seal 39 sealingly engages the inner surface 21 of rim wall 17 and such that the sealing end 40 of seal 39 is elastically bent upwardly thereby to insure that the end of the seal is biased to remain in positive sealing engagement with the inner face of rim 17. In this manner, the interface between the liner and the tray is effectively sealed so as to prevent joint fluid from above from migrating between the liner and the tray. As previously noted, flange 35 extends out beyond the sidewall of liner 27 a distance sufficient (e.g., about one millimeter or so) such that the end 40 of the seal sealingly engages the inner surface of wall 21, as shown in FIGS. 5 and 9C. Because the seal 39 is flexible, it will accommodate variations in differences between the nominal dimensions of the inner tapered surface 21 of rim wall 17 and liner 27.

While seal 39 is preferably a single seal, as shown in the drawings, it will be understood that a double seal (i.e., two seals 39 generally parallel to one another and positioned in close proximity to one another with a slight space therebetween) may be used. This double seal arrangement may provide addition sealing integrity, but it would make it somewhat more difficult for the surgeon to insert the liner into the tray recess. Further, while seal 39 is shown to be integral (made in one piece) with liner 27, it will be understood that within the broader aspects of this invention, the seal 37 may be non-integral (i.e., made separate from the liner and/or made of the same or of a different material than the liner).

Also, with groove 43 below the seal, the groove is preferably positioned immediately above flange 35 such that the flange is somewhat flexible as the liner is forced downwardly into the recess 17 of tray 3. This aids in allowing the liner to be installed in the tray with somewhat less force. Further, although seal 39 has been described as being part of the liner 27, seal 39 could alternatively be a part of the rim wall 15.

Although the locking flanges 35 have been depicted in the preferred embodiment as positioned near the under surface of the liner, they could also function effectively to lock the liner into a corresponding groove provided at the mid or upper portion of the tray rim. Still further, those skilled in the art will appreciate that the locking flange 35 may be positioned above seal 39 so that the seal is located immediately above the bottom surface 11 of tray 3. In addition, the locking flange 35 is shown to be a single tab or flange extending over the end portion of the liner. However, it will be understood that the locking flange could be formed as multiple tabs that press-fit into groove 23 in the rim wall of the tray, or they could be similar to the preferred embodiment, configured as tabs on the front and back ends of the tray that slide into the slot located in the back portion of the rim and press into the slot in the front of the rim.

Although the sealing surface of the tray 3 (i.e., the inner face 21 of rim wall 15) is depicted as smooth and tapered, it could also be straight (perpendicular to recess base 5), rippled or have small ridges and still allow the flexible sealing ridge to achieve a tight seal.

In its preferred embodiment, liner 27 is provided with two locking tabs or flanges 35, one on its anterior end and the other on its posterior end where the major dimension of the liner extends from the anterior to the posterior of the tray 3. While the liner 27, as above described, has the locking tabs or flanges 35 on the opposite anterior and posterior ends, within the broader aspects of this invention, it will be understood that the locking tabs or flanges are only provided on opposite sides or ends and not on all sides or ends. This aids in allowing the liner to be snap-locked secured with respect to the tray without requiring undue force for insertion of the liner.

Specifically, these tabs 35 have a generally rectangular cross sectional shape, but (as previously noted) the lower edge is beveled or chamfered, as indicated at 37, to aid insertion into the tray. These tabs or flanges 35 are situated to fit into matching slots or grooves 23 at the anterior and posterior ends of the recess in the tray, and the tabs are placed so that they will firmly hold the liner firmly against the tray. As the liner is inserted in the tray from front-to-back, the locking tab 35 on the rear or posterior end of the liner is inserted into the posterior groove 23. Then the anterior end of the liner is pressed by the surgeon downwardly on its front surface and the anterior locking tab 35 is deformed (bent) sufficiently to allow it to pass over the sealing surface 21 and come i into register with the slot or groove 23 in the front wall of the tray's rim. Once the front tab 35 is in register with the front slot, the front locking tab 35 elastically returns to its original shape, thus positively engaging the slot and preventing the liner from being easily elevated from the surface of the tray.

It will be noted that the snap lock securement mechanism of the liner within the tray recess (i.e., tabs 35 and grooves 23) is separate from the sealing mechanism (i.e., seal 39 sealingly engaging rim surface 21), and securement mechanism serves to firmly hold the liner within the tray so that the seating surfaces between the polyethylene liner and metal tray remain firmly apposed. Since its purpose is to prevent motion between the polymer liner and metal tray, the locking tabs must be stiff, and therefore cannot act as an effective sealing mechanism. Yet another reason why the snap lock mechanism cannot seal the interface between the polymer liner and metal tray stems from anatomical limitations during surgery. Since the collateral ligament is still intact in most cases of unicompartmental knee replacement, the tibial surface cannot be delivered from under the femoral surface. Therefore, the polymer liner must be inserted from front-to-back and cannot be set directly on top of the metal tray and then pressed into the tray. Therefore the locking tabs 35 on the liner 27 cannot be positioned on the medial and lateral sides of the liner component, and thus cannot form an effective seal. The seal 39 is provided to prevent migration of fluid and debris between the metal tray and liner. The snap lock arrangement provides a positive mechanical engagement between the liner and the metal tray and thus provides a tactile indication to the surgeon that complete and proper seating of the liner into the metal tray has been accomplished. Further, this snap lock mechanism firmly locks the liner in place within the tray and thus prevents toggling and slipping of the interfaces of the two parts under normally expected anatomical loads.

Further, in the preferred embodiment, seal 39 is preferably (but not necessarily) an integral part of liner 27. As previously described, the seal is an integral flexible ridge protruding from the outer wall 28 of the liner and thus cannot serve as the interlock mechanism because it must be flexible to create an effective seal. It will be further understood that while the inner surface 21 of the tray rim 15 is smooth, within the broader aspects of this invention surface 21 need not be smooth so long as the seal 39 is able to form a seal with respect to this rim surface.

As noted, groove 23 and locking tabs 35 are preferably provided only at the major dimensions ends of the tray recess and the liner 27. The reason for this is that if the locking tabs were also present along the minor dimension sides of the liner, the force required of the surgeon to insert the liner within the tray would be too great. It will be understood that the groove may be cut into the rim around the entire perimeter of the rim wall, but if the locking flanges 35 are provided at the major dimension ends of the liner such that the groove along the minor dimension sides of the tray are not used for securement purposes, then effectively, the groove and locking flanges are only provided at the major dimension ends of the tray and liner.

It should be further recognized that the liner and the metal component (e.g., the tibial tray of a knee replacement system or the acetabular cup of a total hip replacement system, or other joint replacement system) of this invention are very accurately dimensioned with respect to one another such that with the liner secured in the tray and with the tray and liner implanted in the patient's body, the liner will fit very tightly within the tray so as to prevent movement of the liner with respect to the tray when the tray and the liner come up to body temperature. This calls for precise dimensions of the liner (which is made of polyethylene) and the tray (which is typically made of titanium) with the dimensions of each component being sized to accommodate differences in the coefficients of thermal expansion of the metal tray and the polyethylene liner as the temperature of both come to body temperature. It was found that the tight dimensional tolerances between the liner and the walls of the tibial tray when at room temperature prevented the used of the continuous seal and the tab/notch arrangement described in my above-noted U.S. Pat. No. 5,766,260 because the liner could not be sufficiently compressed by the surgeon to allow the seal to be made continuously around the liner and to effect substantially snap-lock engagement of the interlock ridge on the liner and a corresponding notch in the liner.

In view of the above, it will be seen that the several objects and features of this invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A component for a joint replacement system comprising:

a tray made of a suitable implantable metal;

said tray having a base and a wall extending upwardly from said base for defining a recess therein, said base having one or more holes therein for receiving bone fixation fasteners for fixation of said tray with respect to said tibia;

a liner of suitable synthetic resin material for securement within said recess after the tray has been surgically affixed to bone, said liner having a shape corresponding generally to the shape of said recess and being sized to have a close fit within said recess;

said tray wall having an inner wall surface which substantially defines the outer periphery of said recess with said inner wall surface tapering inwardly and downwardly toward said base tray;

said inner wall surface having an undercut groove;

said liner having a side wall which is sized with respect to said tray wall so as to fit closely within said inner wall surface, wherein with said liner installed in said recess of said tray;

said liner side wall having a continuous seal extending around its periphery, said seal sealingly engaging said inner wall surface when said liner is installed within said recess thereby to prevent the migration of joint fluid and/or debris past said seal into communication with said holes in the base of the tray; and said liner further having opposite ends and opposite sides and having at least one locking tab on each of said opposite ends or on each of said opposite sides, said locking tabs being integral with said liner and being engageable with said groove in said inner wall surface thereby to snap-lock said liner within said tray as the liner is inserted into said tray by a surgeon after the tray has been surgically affixed to said bone.

2. A component for a joint replacement system as set forth in claim 1 wherein said tray and said liner are of a complimentary non-circular shape, wherein said non-circular shape has a major and a minor dimension, wherein said grooves within said wall are located only along opposite ends of said recess, and wherein said locking tabs are located only along opposite ends of said liner.

3. A component for a joint replacement system as set forth in claim 2 wherein said non-circular liner and said non-circular tray have major and minor dimensions, and wherein said grooves in said tray and said tabs on said liner are located only at the major dimension ends thereof.

4. A component for a joint replacement system as set forth in claim 1 wherein said liner and said inner wall surface are dimensioned with respect to one another such that with said liner installed within said tray and with said tray and said liner at body temperature, said liner is securely held within said recess by said tray wall so as to substantially eliminate movement of the liner with respect to said tray upon subjecting said tibial component to biomechanical loads during normal use of said joint replacement system.

5. A component for a joint replacement system as set forth in claim 1 wherein said seal is integral with said liner and is in flexible sealing engagement with said recess.

6. A joint replacement component for use in a joint replacement system comprising:

(a) a tray;

(b) said tray including at least one screw hole formed therein, said screw holes receiving a bone screw for fixation of said tray to a bone;

(c) said tray having an elevated wall extending completely around its periphery defining a recess, said wall having an inner face;

(d) said wall inner face having one or more locking grooves therein at opposite ends or sides thereof;

(e) said wall having a sealing surface on its inner face spaced outwardly from said locking grooves;

(f) a liner configured to be received within said tray, said liner having a sidewall; and (g) wherein said liner includes:

(i) at least one peripheral flexible seal extending outwardly from and extending continuously around said liner side wall;

(ii) wherein with said liner received within said recess, said seal sealingly engaging said inner face of said wall so to restrict migration of debris and joint fluid toward said at least one screw hole; and (iii) said liner further having opposite ends and opposite sides and having at least one locking lug on each of said opposite ends or on each of said opposite sides for snap lock reception within said locking grooves in said wall thereby to permit a surgeon to insert said liner within said tray from the front, side or back after the tray has been surgically affixed to the desired skeletal structure substantially without interference with surrounding tissue or ligaments.

7. A component as set forth in claim 6 wherein said tray recess and said liner each are of a non-circular shape having corresponding major and minor dimensions, and wherein said locking grooves are located substantially contiguously with the bottom surface of said recess, and are located at only the major dimension ends of said wall.

8. A component as set forth in claim 6 wherein said inner face is located on the inner surface of said peripheral wall.

9. A component as set forth in claim 6 wherein said flexible seal is integral with the liner.

10. A component as set forth in claim 9 wherein said flexible seal has a sealing end adapted to sealingly engage said inner face of said wall.

11. A component as set forth in claim 10 wherein said flexible seal is of decreasing cross section from the body of said liner to said sealing end.

12. An orthopedic implant component for affixation to a skeletal structure comprising:

a tray made of a suitable implantable metal;

said tray having a base and a wall extending upwardly from said base for defining a recess therein, said base having one or more holes therein for receiving bone fixation fasteners for fixation of said tray with respect to said skeletal structure;

a liner of suitable synthetic resin material for securement within said recess after the tray has been surgically affixed to the skeletal structure, said liner having a shape corresponding generally to the shape of said recess and being sized to have a close fit within said recess;

said tray wall having an inner wall surface which substantially defines the outer periphery of said recess with said inner wall surface tapering inwardly and downwardly toward said base;

said inner wall surface having an undercut groove therein;

said liner having a side wall which is sized with respect to said tray wall so as to fit closely within said inner wall surface;

wherein with said liner installed in said recess of said tray, said liner side wall having a continuous seal formed integrally with said liner, said seal sealingly engaging said inner wall surface when said liner is installed within said recess thereby to prevent the migration of joint fluid and/or debris past said seal into communication with said holes in the base of the tray; and said liner further having opposed sides and having at least one locking tab on one of said opposed sides, said at least one locking tab being integral with said liner and being engageable with said grooves in said inner wall surface thereby to snap-lock said liner within said tray as the liner is inserted into said tray by a surgeon after the tray has been surgically affixed to the skeletal structure.

13. An orthopedic implant component as set forth in claim 12 wherein said tray is of a non-circular shape and has a major and a minor dimension, and wherein said locking tabs are located only at the major dimension ends of said liner.

14. An orthopedic implant component as set forth in claim 12 wherein said liner and said inner wall surface are dimensioned with respect to one another such that with said tray and said liner at body temperature said liner is securely held within said tray wall so as to substantially eliminate movement of the liner with respect to said tray upon subjecting said skeletal structure component to biomechanical loads during normal use of said orthopedic implant component.

* * * * *